(12) United States Patent
Yodfat et al.

(10) Patent No.: US 8,603,075 B2
(45) Date of Patent: Dec. 10, 2013

(54) FLUID DELIVERY SYSTEM WITH ELECTROCHEMICAL SENSING OF ANALYTE CONCENTRATION LEVELS

(75) Inventors: Ofer Yodfat, Maccabim-Reut (IL); Gavriel J. Iddan, Haifa (IL); Ruthy Kaidar, Haifa (IL); Gali Shapira, Haifa (IL)

(73) Assignee: Medingo, Ltd., Yoqneam Illit (IL)

( * ) Notice: Subject to any disclaimer, the term of this patent is extended or adjusted under 35 U.S.C. 154(b) by 565 days.

(21) Appl. No.: 11/989,665

(22) PCT Filed: Sep. 25, 2007

(86) PCT No.: PCT/IL2007/001177
§ 371 (c)(1),
(2), (4) Date: May 26, 2010

(87) PCT Pub. No.: WO2008/038274
PCT Pub. Date: Apr. 3, 2008

(65) Prior Publication Data
US 2010/0241086 A1 Sep. 23, 2010

Related U.S. Application Data

(60) Provisional application No. 60/848,511, filed on Sep. 29, 2006.

(51) Int. Cl.
*A61K 9/22* (2006.01)
*A61M 5/00* (2006.01)
*C12M 1/00* (2006.01)

(52) U.S. Cl.
USPC ............... 604/890.1; 604/246; 204/403.01

(58) Field of Classification Search
USPC ........................................ 604/890.1
See application file for complete search history.

(56) References Cited

U.S. PATENT DOCUMENTS

| | | | |
|---|---|---|---|
| 4,680,268 A | 7/1987 | Clark, Jr. | |
| 4,705,503 A | 11/1987 | Dorman | |
| 5,109,850 A * | 5/1992 | Blanco et al. | 600/368 |
| 5,237,993 A * | 8/1993 | Skrabal | 600/309 |
| 5,800,420 A | 9/1998 | Gross et al. | |

(Continued)

FOREIGN PATENT DOCUMENTS

| | | |
|---|---|---|
| EP | 0 134 758 A | 3/1985 |
| WO | WO 01/13784 | 3/2001 |

OTHER PUBLICATIONS

DCCT Trial Research Group, "The Effect of Intensive Treatment of Diabetes on the Development and Progression of Long-Term Complications in Insulin-Dependent Diabetes Mellitus", *N. E. J. Med.*, 329:977-986 (1993).

(Continued)

*Primary Examiner* — Jason Flick
(74) *Attorney, Agent, or Firm* — Mintz, Levin, Cohn, Ferris, Glovsky and Popeo, P.C.

(57) ABSTRACT

A system and a method for delivering fluid to and sensing analyte levels in the body of the patient are disclosed. The system includes a dispensing apparatus configured to infuse fluid into the body of the patient and a sensing apparatus configured to be in communication with the dispensing apparatus and further configured to detect a level of analyte concentration in the body of the patient upon diffusion of the analyte into the fluid to be dispensed by the dispensing apparatus.

19 Claims, 11 Drawing Sheets

(56) References Cited

U.S. PATENT DOCUMENTS

| | | | |
|---|---|---|---|
| 6,091,976 | A | 7/2000 | Pfeiffer et al. |
| 6,809,653 | B1 | 10/2004 | Mann et al. |
| 6,862,465 | B2 | 3/2005 | Shults et al. |
| 6,881,551 | B2 | 4/2005 | Heller et al. |
| 6,892,085 | B2 | 5/2005 | McIvor et al. |
| 6,975,893 | B2 | 12/2005 | Say et al. |
| 7,389,133 | B1 | 6/2008 | Kotulla et al. |
| 2003/0130616 | A1 | 7/2003 | Steil |
| 2003/0212379 | A1 | 11/2003 | Bylund |
| 2004/0074785 | A1 | 4/2004 | Holker et al. |
| 2005/0107743 | A1 | 5/2005 | Fangrow |
| 2005/0131346 | A1 | 6/2005 | Douglas |
| 2005/0272989 | A1 | 12/2005 | Shah et al. |
| 2006/0036145 | A1* | 2/2006 | Brister et al. ............ 600/345 |
| 2006/0253085 | A1 | 11/2006 | Geismar et al. |
| 2006/0253086 | A1 | 11/2006 | Moberg et al. |
| 2007/0106218 | A1 | 5/2007 | Yodfat et al. |
| 2009/0062767 | A1 | 3/2009 | Van Antwerp et al. |
| 2010/0100077 | A1* | 4/2010 | Rush et al. ............ 604/890.1 |

OTHER PUBLICATIONS

Maran et al., "Continuous Subcutaneous Glucose Monitoring in Diabetic Patients", *Diabetes Care*, 25(2):347-352 (2002).

Mastrototaro, J. J., "The MiniMed Continuous Glucose Monitoring System", *Diabetes Tech. Therapeutics*, 2(Suppl. 1):13-18 (2000).

Nathan et al., "Intensive Diabetes Treatment and Cardiovascular Disease in Patients with Type 1 Diabetes", *N.E. J. Med.*, 353(25):2643-2653 (2005).

UKPDS Group Trial, "Tight blood pressure control and risk of macrovascular and microvascular complications in type 2 diabetes: UKPDS 38", *BMJ*, 317:703-713 (1998).

UKPDS Trial, "Intensive blood-glucose control with sulphonylureas or insulin compared with conventional treatment and risk of complications in patients with type 2 diabetes (UKPDS 33)", Lancet, 352:837-853 (1998).

Wang, J., "Glucose Biosensors: 40 Years of Advances and Challenges", 13(12):983-988 (2001).

Wentholt et al., "Comparison of a Needle-Type and a Microdialysis Continuous Glucose Monitor in Type 1 Diabetic Patients", *Diabetes Care*, 28(12):2871-2876 (2005).

Park et al., "Electrochemical non-enzymatic glucose sensors", *Anal. Chimica Acta.*, 556:46-57 (2006).

Valdes et al., "In Vitro and In Vivo Degradation of Glucose Oxidase Enzyme Used for an Implantable Glucose Biosensor", *Diabetes Tech. Therapeutics*, 2(3):367-376 (2000).

International Search Report, PCT Application No. PCT/IL2007/001177.

\* cited by examiner

FLUID DELIVERY SYSTEM WITH ELECTROCHEMICAL SENSING OF ANALYTE CONCENTRATION LEVELS

CROSS REFERENCE TO RELATED APPLICATIONS

This application is a national stage entry of PCT/IL07/001177, having an international filing date of Sep. 25, 2007, which claims priority to U.S. provisional patent application No. 60/848,511, filed Sep. 29, 2006. Each of the foregoing disclosures is expressly incorporated herein in its entirety.

FIELD OF INVENTION

The present invention relates generally to a device and a method for monitoring of body analytes and dispensing of fluids (at least one of monitoring and dispending being continuous, or, alternatively, both functions being continuous). Particularly, the invention refers to continuous dispensing insulin and monitoring glucose levels. Even more particularly the invention refers to an electrochemical based continuous subcutaneous glucose monitoring system, coupled with an insulin delivery system.

BACKGROUND OF THE INVENTION

Diabetes and Glycemic Control

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. The normal pancreatic islet cells (beta cells) continuously sense the blood glucose levels and consequently regulate insulin secretion to maintain near constant levels.

Much of the burden of the disease to the patient and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). There is now good evidence that morbidity and mortality of diabetic patients is related to the duration and severity of hyperglycemia [DCCT Trial, N. Engl. J. Med. 1993; 329: 977-986, UKPDS Trial, Lancet 1998; 352: 837-853. BMJ 1998; 317, (7160): 703-13 and the EDIC Trial, N. Engl. J. Med. 2005; 353, (25): 2643-53]. In theory, returning blood glucose levels to normal by hormone replacement therapy using insulin injections and/or other treatments in diabetes should prevent complications, but, frustratingly, near-normal blood glucose concentrations are very difficult to achieve and maintain in many patients, particularly those with type 1 diabetes. In these patients, blood glucose concentration can swing between very high (hyperglycemia) and very low (hypoglycemia) levels in an unpredictable manner. Thus, in order to achieve tight glycemic control, the two functions of the normal pancreas should be substituted for—glucose monitoring and insulin delivery. Furthermore, a closed loop system having a feedback mechanism connecting both functions (often referred to as an "artificial pancreas") could theoretically maintain near normal blood glucose levels.

Glucose Monitoring

Most diabetic patients currently measure their own blood glucose several times during the day by obtaining finger-prick capillary samples and applying the blood to a reagent strip for analysis in a portable glucose meter. The discomfort involved with these tests leads to poor patient compliance. Testing cannot be performed while sleeping and while the subject is occupied. In addition, the results do not give information regarding the trends in glucose levels, but rather provide only discrete readings, taken at large time intervals from one another. Therefore continuous glucose monitoring is advantageous, providing essentially continuous glucose readings by performing discrete measurements, at a very high rate.

Today, most electrochemical glucose sensors are enzyme-based. The detection principle of these sensors is based on the monitoring of the enzyme-catalysed oxidation of glucose. These include glucose sensors using amperometric or potentiometric operating principles (hydrogen-peroxide electrode based, oxygen-electrode based, mediator-based and potentiometric-electrode based).

The enzymatic reaction that occurs in the majority of these sensors is catalyzed by glucose oxidase (GOX). In this reaction, oxygen and glucose yield gluconic acid and hydrogen peroxide according to the following reaction:

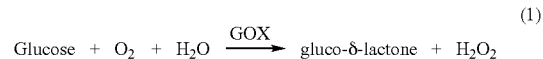

(1)

In this reaction, in which glucose is oxidized to gluconic acid, glucose oxidase acts temporarily as an electron acceptor, which means that it is first reduced to an inactive state and subsequently reactivated by the reduction of oxygen to hydrogen peroxide.

The analyte concentration is transduced into a detectable signal, generally by using potentiometric or amperometric methods.

Potentiometric electrodes measure the equilibrium potential between an indicating electrode and a stable reference electrode under zero current conditions. The electrode can be ion selective (ISE)—for instance, a pH electrode. In the GOX reaction, the product gluconic acid changes the local pH:

Amperometric electrodes operate in non-equilibrium conditions. The transducer consists of a working electrode, where electrochemical oxidation or reduction takes place, and a reference electrode. The intensity of the current is a function of the electro-active substance. A major difference of the amperometric electrode from the potentiometric electrode is the consumption of reaction products. Different species of the reaction may be determined amperometrically:

a. Hydrogen peroxide ($H_2O_2$) electrode based glucose sensor. This type of glucose sensor measures the amount of $H_2O_2$ produced in the conversion of glucose by GOX by an amperometric hydrogen-peroxide electrode.

(2)

b. Oxygen electrode based glucose sensor. A glucose sensor that measures the amount of oxygen consumed during the enzymatic oxidation of glucose.

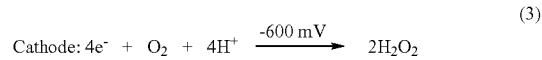

(3)

Catalase, an enzyme that catalyzes the decomposition of hydrogen peroxide into water and oxygen, may be co-immobilised in excess to prevent peroxide-mediated GOX inactivation.

$$2H_2O_2 \xrightarrow{catalase} 2H_2O + O_2 \quad (4)$$

c. Mediator based glucose sensor. This type of glucose sensor uses an artificial electron acceptor, or mediator, to replace the natural acceptor, oxygen, in the oxidation of glucose by glucose oxidase.

Glucose+glucose oxidase(ox)→gluconic acid+glucose oxidase(Red)

glucose oxidase(Red)+mediator(ox)→glucose oxidase (ox)+mediator(Red)

electrode: mediator(Red)→mediator(ox)

ox-oxidized form; Red-reduced form

The mediator approach is not oxygen dependent. The oxidation of the reduced mediator occurs at a low potential, thus, reducing the sensitivity of the sensor to interfering substances. Many commercial blood glucometers use mediator-based enzyme strips. Common mediators used are ferricyanide and ferrocene. (Electroanalysis 2001, Vol. 13, No. 12, pp. 983-987)

Most in-vivo devices are mediatorless due to possible leaching and toxicity of the mediator. These devices rely on oxygen, as a physiological electron acceptor. Arterial blood has a glucose to oxygen ratio of approximately 10 to 1; venous blood has a ratio of about 100 to 1. Thus, in vivo devices use membranes to tailor the flux of glucose and oxygen to the enzymatic coating on the electrode. Different layers alter the diffusion of one or more analytes into the area that comprises the catalytic enzyme or enzymes.

The Guardian® RT Continuous Glucose Monitoring System, developed by Medtronic MiniMed Inc, is a GOX-based sensor (as discussed in U.S. Pat. No. 6,892,085). The sensor consists of a subcutaneously implanted, needle-type, amperometric enzyme electrode, coupled with a portable logger (Diab. Tech. Ther. 2000; 2: Supp. 1, 13-18). The sensor is based on the well known technology of GOX immobilized at a positively charged base electrode, with electrochemical detection of hydrogen peroxide production. A conventional sensor having layered structure is discussed in U.S. Published Patent Application N. 2005/0272989 to Shah. The following layers are disposed in the described order: A base layer to support the sensor, a conductive layer which comprises at least one electrode, an analyte sensing layer which comprises the enzyme, a protein layer (albumin) which may stabilize the enzyme, an adhesion promoting layer to promote adhesion between adjoining layers, an analyte modulating layer which regulates analyte contact with the analyte sensing layer, and an insulating layer. The analyte modulating layer may prevent or restrict the diffusion of glucose, while at the same time facilitates the diffusion of oxygen.

U.S. Pat. No. 6,975,893 to Say, assigned to TheraSense, Inc. (now, Abbott Laboratories), and U.S. Pat. No. 6,862,465 to Shults, assigned to Dexcom, discuss a conventional layer permeable to oxygen and impervious to glucose which covers most of the working electrode and a layer of smaller area which is permeable to glucose. In this configuration, glucose can only enter through the small exposed area while oxygen has a much larger surface to diffuse through.

The Freestyle Navigator™ is a GOX-based sensor, discussed in U.S. Pat. No. 6,881,551 to Heller assigned to Abbott Laboratories, formerly TheraSense, Inc. This sensor is placed just under the skin by a disposable self-insertion device. Information is communicated wirelessly between the transmitter and the receiver every minute. The receiver is designed to display glucose values, directional glucose trend arrows, and rate of change. The receiver also has high and low glucose alarms, and stores glucose data for future analysis.

U.S. Pat. No. 6,862,465 to Shults and U.S. Published Patent Application No. 2006/0036145 to Brister, both assigned to DexCom, discuss conventional long-term and short-term GOX-based continuous glucose monitoring systems. Both systems include a sensor, a small insertable or implantable device that continuously measures glucose levels in subcutaneous tissue, and a small external receiver to which the sensor transmits glucose levels at specified intervals. The receiver displays the patient's current blood glucose value, as well as 1-hour, 3-hour and 9-hour trends. The receiver also sounds an alert when an inappropriately high or low glucose excursion is detected.

The DexCom™ STS™ Continuous Glucose Monitoring System is a user insertable short-term sensor that is inserted just under the skin where it is held in place by an adhesive. Once inserted the user would wear the sensor for up to three days before being replaced. After three days, the user removes the sensor from the skin and discards it. A new sensor can then be used with the same receiver. The DexCom™ STS™ Continuous Glucose Monitoring System has been FDA-approved. The DexCom™ Long Term Sensor is implanted under the skin in the abdomen via a local anesthetic short outpatient procedure by a physician and is designed to function for up to one year. At the end of its life, the sensor can be removed by a physician in a short procedure, and another sensor implanted.

Microdialysis is an additional conventionally-available technology (Diab. Care 2002; 25: 347-352) and an example of it is discussed in U.S. Pat. No. 6,091,976 to Pfeiffer, assigned to Roche Diagnostics, and commercially available as a Menarini Diagnostics GlucoDay® S device. A fine, semipermeable hollow dialysis fiber is inserted into the subcutaneous tissue and perfused with isotonic fluid. Glucose diffuses across the semi-permeable fiber, which is pumped outside the body via the microdialysis mechanism for measurement by a glucose oxidase-based electrochemical sensor. Initial reports (Diab. Care 2002; 25: 347-352) show good agreement between sensor and blood glucose readings, and good stability with a one-point calibration over one day. Higher accuracies were found when using the microdialysis-based sensor, compared to the needle-type sensor (Diab. Care 2005; 28, (12): 2871-6).

Under development are mediator-free and membrane-free glucose biosensors. In these biosensors, electrons are directly transferred from the enzyme to the electrode, overcoming the fact that natural glucose oxidase does not directly transfer electrons to conventional electrodes because a thick protein layer surrounds its redox center. A nanoporous platinum electrode has been showing good sensitivity and selectivity in trials (Analytica Chimica Acta 556, 2006, p. 46-5'7).

The enzymatic reaction that occurs in GOX-based sensors consumes oxygen and glucose to yield gluconic acid and hydrogen peroxide. This leads to numerous disadvantages inherent to glucose monitors employing such reaction, including:

GOX-based devices rely on the use of oxygen as the physiological electron acceptor, thus, the stoichiometric limitation of oxygen in vivo is a major shortcoming. In addition, these devices are subject to errors due to fluctuations in the concentration of dissolved oxygen.

Application of mediators as an artificial electron acceptor to replace the natural acceptor, oxygen, in the oxidation of glucose by glucose oxidase is problematic when used in vivo due to potential leaching and toxicity of the mediator.

The amperometric measurement of hydrogen peroxide requires application of a potential at which additional electroactive species exist, e.g., ascorbic and uric acids or acetaminophen. These and other oxidizable constituents of biological fluids can compromise the selectivity and hence the overall accuracy of the glucose concentration measurement.

Hydrogen peroxide is known for its toxic effects compromising the biocompatibility of the sensor. This poses a problem mainly when the hydrogen peroxide is not consumed for the transduction (that is, when the biosensor is not based on hydrogen peroxide). As mentioned above, application of catalase may resolve this setback.

Hydrogen peroxide deactivates the GOX molecules, limiting the time available for application of the sensor. Overloading the sensor with an excess of enzyme, more than what is required to catalyze the incoming glucose, may be helpful in overcoming this problem. Here too, co-immobilization of catalase may be beneficial. However, this solution is more appropriate for glucose sensors based on the detection of $O_2$ that do not depend on measuring $H_2O_2$. Furthermore, catalase is in turn inactivated by hydrogen peroxide (Diab. Tech. & Ther., Vol. 2, No. 3, 2000, pp. 367-376).

The size of the cannula, including the sensing unit with its various layers, is relatively large, affecting the ease and comfort of the cannula insertion into the user's body. Miniaturizing the sensing technology within the cannula, which requires high levels of enzyme loading while keeping high measurement sensitivity, remains a challenge. This naturally does not pose a problem when the sensor is located outside the body.

Disadvantages of the microdialysis-based glucose sensors stem primarily from the fact that these systems involve the constant perfusion of solution through the microdialysis probe. This operational method requires the presence of a dedicated pump and reservoir, leading to large and bulky devices, and also necessitates high energy consumption. Furthermore, the relatively large size of the microdialysis catheter often causes a wound and subsequent local tissue reactions, following its insertion into the subcutaneous tissue. Finally, the microdialysis process generates long measurement lag times, due to the essential slow perfusion rates and long tubing.

The devices currently being marketed, manage to overcome the major drawbacks of the $H_2O_2$ toxicity and the limited oxygen supply, by the use of peroxidase-based sensors with an excess of enzyme, and the application of a combination of layers. Different membranes are used to tailor the flux of glucose and oxygen to the enzymatic coating on the electrode, accordingly.

Closed-Loop Systems

Continuous glucose monitors alone are not sufficient for balanced diabetes management. In order to achieve tight glycemic control, the two functions of the normal pancreas, glucose sensing and insulin delivery, should both be substituted. A closed loop system provided with a feedback mechanism could theoretically maintain near normal blood glucose levels. Such a closed loop system, referred to as an "artificial pancreas", consists of an insulin pump and a continuous glucose sensor that work together to mimic the human pancreas. The continuous glucose sensor reports the measured glucose values to the insulin pump, which then calculates the appropriate dosage of insulin and delivers it to the user's body.

The existing artificial pancreatic systems contain a sensor and pump which are two discrete, expensive components, with separate housing. These systems are both relatively bulky and heavy devices which should be attached to the user's belt or skin. In addition, the two devices require two infusion sets with long tubing and two insertion sites, consequently extending the system's insertion and disconnection times and substantially increasing adverse events like infections, irritations, bleeding, etc.

The present invention relates to a system, method and apparatus that overcome the drawbacks of the prior art, presenting a skin adhered patch which is discreet and free of noticeable tubing. In addition, some embodiments of the present invention are relatively low cost for the user and highly profitable for the manufacturer and insurer due to a combination of a disposable part and a reusable part described in more detail later on.

Accordingly, there is a need for a device that monitors glucose levels and concomitantly delivers insulin which is a miniature, one piece device, discreet, economical for the users and highly cost effective for the payer.

There is also a need for a closed loop system that monitors glucose levels and dispenses insulin according to the sensed glucose levels, which is a miniature single device, discreet, economical for the users and highly cost effective for the payer.

There is also a need to dispense insulin and monitor glucose using a single subcutaneous cannula avoiding double skin pricking with every system replacement.

There is also a need for a miniature single device, discreet, economical for the users and highly cost effective for the payer, subcutaneously implanted, continuous glucose monitor, coupled with an insulin delivery pump, based on electrochemical measurement means.

There is also a need for a device that senses analyte concentration within a subcutaneous cannula by electrochemical means, which is a miniature single device, discreet, economical for the users and highly cost effective for the payer.

There is an alternative need to electrochemically sense subcutaneous ISF analyte concentration levels with a sensor located above the user's skin and a method to transport fluid containing the ISF analyte from the body to said sensor.

There is also a need to electrochemically sense subcutaneous ISF analyte concentration levels above the user's skin by a fluid transport mechanism, in a device that concomitantly dispenses insulin.

SUMMARY OF THE INVENTION

It is an object of some of the embodiments of the present invention to provide a device that continuously dispenses fluids into the body and monitors analyte levels.

It is an object of some of the embodiments of the present invention to provide a device that continuously dispenses insulin and monitors glucose levels.

It is an object of some of the embodiments of the present invention to provide a device that dispenses insulin according to continuously monitored glucose levels enabling a closed loop system.

It is an object of some of the embodiments of the present invention to provide a miniature skin adhered device that dispenses insulin and monitors glucose.

It is an object of some of the embodiments of the present invention to provide a skin adhered patch that dispenses insulin and monitors glucose.

It is an object of some of the embodiments of the present invention to provide a device that dispenses insulin and monitors glucose using a single subcutaneous cannula.

It is an object of some of the embodiments of the present invention to measure analyte concentration levels essentially continuously, by performing discrete measurements, at a high measurement rate with short inter-measurement intervals.

It is an object of some of the embodiments of the present invention to detect analyte concentration levels in the body using electrochemical detection means.

It is an object of some of the embodiments of the present invention to detect analyte concentration levels in the body using electrochemical means, suitable for direct monitoring subcutaneous ISF fluid, located below the skin.

It is an object of some of the embodiments of the present invention to detect analyte concentration levels in the body using electrochemical means, suitable for direct monitoring subcutaneous ISF fluid, located inside the dispensing cannula.

It is another object of some of the embodiments of the present invention to detect analyte concentration levels in the body using electrochemical means, suitable for direct monitoring subcutaneous ISF fluid, located above the skin and a means to transport said fluid.

It is an object of some of the embodiments of the present invention to provide a device that includes a disposable part and a reusable part. The reusable part is configured to include relatively expensive components and the disposable part is configured to include relatively cheap components, thus, providing a low cost product for the user and a highly profitable product for the manufacturer and payer.

Some of the embodiments of the present invention are directed to a closed loop system that regulates body analyte concentration by concomitantly monitoring analyte levels and dispensing a fluid, e.g., a drug that can adjust the said analyte levels.

Some of the embodiments of the present invention are directed to a skin adhered device, capable of chemically reacting with an endogenous substance, allowing the monitoring of analyte concentrations by electrochemical means. In some embodiments, the chemical reaction is enzyme-based.

In some embodiments, the device includes a dispensing apparatus and a sensing apparatus. The dispensing apparatus can be configured to be used for infusing fluid into the body of a user. The sensing apparatus can also be configured to detect analyte concentration levels in the body.

In some embodiments, the dispensing apparatus and the sensing apparatus can be configured to work in a closed loop system, where a processor-controller apparatus regulates the dispensing of fluid according to the sensed analyte concentration.

In some embodiments, the dispensing apparatus and the sensing apparatus may work in a semi-closed loop system, where a processor-controller apparatus regulates the dispensing of fluid according to the sensed analyte concentration and according to external user inputs.

In some embodiments, the device includes two remotely controlled units, one unit containing the sensing apparatus and another unit containing the dispensing apparatus. The loop is closed by transmittance of information from the sensing apparatus to the dispensing apparatus, which adjusts delivery of the fluid accordingly.

In some embodiments, the device includes a single unit that contains only a sensing apparatus. Thus, the device is a continuous analyte (e.g., glucose) monitoring system.

In some embodiments, the device includes two parts, a reusable part that contains all electronic and driving elements, and a disposable part, that contains the fluid reservoir and the needle assembly.

In some embodiments the monitored analyte is glucose.

In some embodiments the dispensed fluid is insulin, to be used with diabetic patients.

In some embodiments, the device comprises a minimally-invasive sensing apparatus, in which detection of the analyte concentration levels is performed in a minimally-invasive manner. In these embodiments, the skin adhered patch can serve as a sensing device and includes a single cannula which is inserted into the subcutaneous tissue and monitors the ISF analyte levels (e.g., glucose).

In some embodiments, the device includes a dispensing apparatus and a minimally-invasive sensing apparatus, in which detection of analyte concentration levels is performed in a minimally-invasive manner.

In other embodiments, the minimally-invasive sensing apparatus uses micropores made in the skin to extract ISF from the body. Such micropores are made by means of laser, ionophoresis or any other methods.

In some embodiments, the minimally-invasive sensing apparatus uses a cannula, inserted into the subcutaneous tissue allowing contact with the ISF.

In some embodiments, the self-adhesive device includes a fluid reservoir, a needle assembly device, a pumping apparatus and an electrochemical sensing apparatus. The reservoir contains fluid, such as isotonic fluid or medication (e.g., insulin). The flow of fluid from the reservoir is controlled by the pumping apparatus and a processor-controller apparatus. The needle assembly includes a cannula and a penetrating member. The penetrating member is used to insert the cannula into the body.

In some embodiments, the cannula includes a semi-permeable membrane enabling diffusion, selectively allowing entry of analyte molecules (e.g., glucose) into the cannula. This space is occupied either by an isotonic dispensed fluid, or by medication (e.g., insulin). The diffusion process, occurring across the semi-permeable membrane, allows analyte molecules (e.g., glucose) to move according to the concentration gradient and rapidly achieve partial or full equilibrium, i.e., the analyte concentration in the fluid within the cannula, is proportional or equal to the analyte concentration in the interstitial fluid (ISF) outside the cannula.

In embodiments where the membrane constructing the cannula is semi-permeable, the analyte (e.g., glucose) diffuses but competing electroactive components of the ISF (e.g., ascorbic acid, uric acid, or acetaminophen) cannot diffuse. Thus, these oxidizable constituents of the ISF do not compromise the selectivity and hence the overall accuracy of the analyte (e.g., glucose) concentration measurement.

In some embodiments, the membrane constructing the cannula is permeable, enabling diffusion, allowing non-selective entry of analyte molecules (i.e., glucose molecules and other molecules contained in the ISF) into the cannula space.

In some embodiments, the sensing of glucose levels and the dispensing of insulin are both done through one single exit port, using a single cannula. In such embodiments, the sensing apparatus and dispensing apparatus share a cannula, a fluid reservoir, and a pump, thus, the device includes a single cannula, a single fluid reservoir and a single pump.

In some embodiments the device has two exist ports. Monitoring analyte (e.g., glucose) levels is done through a first exit port (a single cannula) and the dispensing of fluid (e.g., insulin) is done through a second exit port, using an additional cannula.

In some embodiments, the sensing apparatus and dispensing apparatus have separate cannulae and associated separate fluid reservoirs. Fluid delivery (pumping) from both reservoirs can be achieved either by one pump or by two separate pumps.

In some embodiments, the pumping mechanism can be peristaltic. Both in the single cannula and in the double cannula configurations, a single peristaltic wheel can dispense fluid through one or more delivery tubes.

In other embodiments, two peristaltic pumps are used, one pump is used with a tube used for fluid delivery, and another pump is used with a tube for analyte levels sensing.

In some embodiments, a pump having a syringe reservoir can be used. In this case, two pumping mechanisms and two syringe reservoirs can be included in the double cannula configuration.

According to an embodiment of the present invention, the sensing apparatus can be based on electrochemical detection. The sensor employed in the sensing apparatus can be based on any of the enzymatic assays known in the art (e.g., GOX, hexokinase, glucose dehydrogenase). Alternatively, the sensing apparatus can include an electrochemical non-enzymatic glucose sensor (e.g., direct oxidation of oxygen on solid state surfaces). Alternatively, the sensing apparatus can include an affinity glucose sensor based on competitive binding of the desired analyte and a labeled analogue to receptor sites specific for the analyte and the labeled ligand.

The sensing apparatus can be configured to utilize a combination of various electrochemical detection methods.

In some embodiments, the sensing apparatus can include an electrochemical sensing unit that has one or more working electrodes (that can be coated with an enzymatic sensing layer), at least one counter electrode, as well as any other electrodes that can be used in the electrochemical process; a measurement cell unit; and various electronic processing units.

In some embodiments, the measurement cell unit can include an analyte-saturated fluid, which can be configured to come in contact with the working electrode within the sensing unit.

The measurement cell unit and the sensing unit can be located either in a portion of the cannula that is located under the user's skin (i.e., within the body of the patient), or in that portion that is located above the skin of the patient, and is outside the body. The configuration, in which the measurement cell unit and sensing unit reside within the body, under skin will be referred to as an "intrinsecus" configuration. The configuration, in which the measurement cell unit and sensing unit reside outside the body, will be referred to as an "extrinsecus" configuration.

In some embodiments, electrochemical glucose sensing can be carried out in an "intrinsecus" configuration. In these embodiments, the measurement cell unit is located within that part of the cannula that is inside the body, and the sensing unit, including one or more of its electrodes, are inserted therein. In the "intrinsecus" configuration embodiments, the measurement cell unit is located within a portion of the cannula that is inside the body, and one or more parts of the sensing unit (e.g., the working electrode), are inserted therein, while one or more parts of the sensing unit (e.g., the control and reference electrodes) are located outside the body.

In some embodiments, electrochemical glucose monitoring can be carried out in the "extrinsecus" configuration. In these embodiments, the measurement cell unit is in a portion of the cannula, which is located above the skin and the sensing unit is also located outside the body, above the skin.

In both "intrinsecus" and "extrinsecus" configurations embodiments, the electronic processing unit of the electrochemical sensing apparatus can be located in the reusable part of the device, and the measurement cell unit and the sensing unit can be located in the disposable part of the device.

DETAILED DESCRIPTION OF THE INVENTION

In some embodiments, the present invention relates to systems, method, and apparatuses for monitoring of body analytes and dispensing of fluids, and in particular, continuous dispensing of insulin and monitoring of patient's glucose blood glucose levels. In some embodiments, the present invention employs a chemical reaction designated by equation (5) below. In equation (5), glucose is oxidized to gluconic acid by glucose oxidase.

(5)

A transformation of the analyte concentration into a detectable signal can be effected using conventionally known potentiometric or amperometic sensors.

Figure 1:
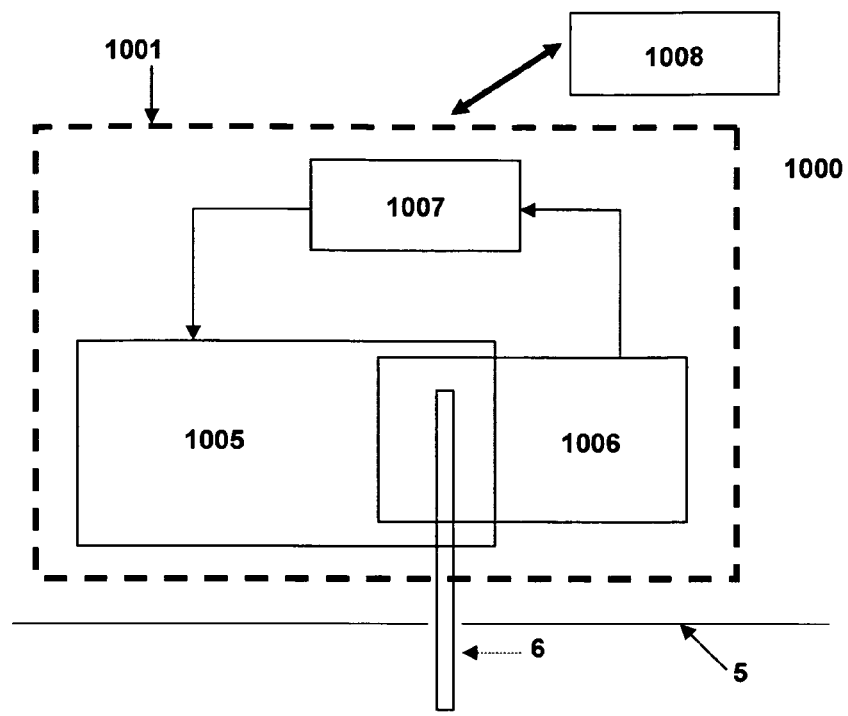
FIG. 1 illustrates an exemplary closed loop system, including the dispensing apparatus, the sensing apparatus, the processor-controller apparatus, and the remote control unit, with a single cannula, according to some embodiments of the present invention.

FIG. 1 illustrates an exemplary embodiment of a system (1000) for dispensing of fluids and monitoring of body analytes, according to the present invention. The present invention's system can be configured to include a dispensing apparatus for dispensing fluids and a sensing apparatus for monitoring of body analytes.

In some embodiments, the dispensing and sensing apparatuses can be embodied in a single device, and can be further configured to use a single cannula for dispensing and sensing. Additionally, both apparatuses can be configured to work as a closed-loop system. FIG. 1 illustrates an exemplary closed loop or semi-closed loop-system (1000) that includes a dispensing apparatus (1005), a sensing, apparatus (1006), a processor-controller apparatus (1007), a remote control unit (1008), and a cannula (6) located under the skin (5) in the subcutaneous tissue. All components, apart from the remote control unit (1008), can be configured to be embodied in a single device (1001), which can be attached to the user's skin by adhesives (not shown in FIG. 1). The remote control unit (1008) can be configured to maintain a bidirectional communication channel with the device (1001) thereby allowing programming, data handling, and user input. A single cannula (6), which includes a permeable or semi-permeable membrane, penetrates the skin of the patient and allows concomitant fluid delivery to the body of the patient. It can be also configured to sense analytes in the body of the patient. In a closed-loop system, the processor-controller apparatus (1007) is configured to receive input data from the sensing apparatus (1006) (e.g., analyte concentration) and, after processing the input data, authorize the dispensing apparatus (1005) to dispense fluid accordingly. In a semi-closed-loop system, the processor-controller apparatus (1007) is configured to receive input data from the patient through the remote control unit (1008).

In other embodiments, the present invention's device includes two parts (not shown in FIG. 1), a reusable part and a disposable part. Each part can be configured to be enclosed in its own housing. Relatively cheap components of the sensing and dispensing apparatuses can reside in the disposable part and relatively expensive components of both apparatuses can reside in the reusable part.

Figure 2:
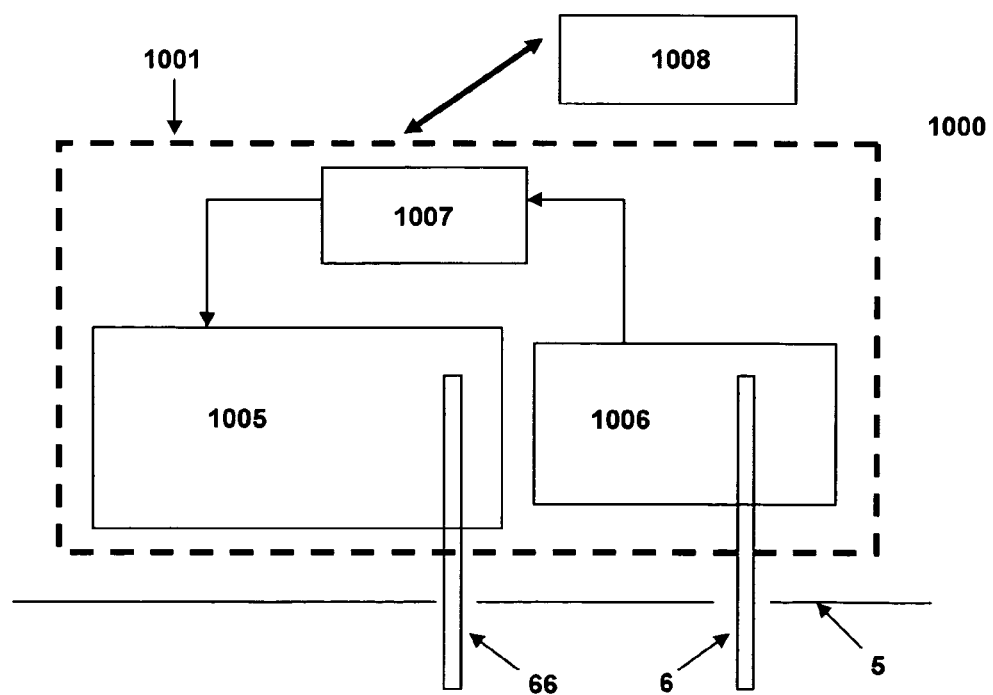
FIG. 2 illustrates an exemplary closed loop system, including the dispensing apparatus, the sensing apparatus, the processor-controller apparatus, and the remote control unit, in which the dispensing and sensing apparatuses have separate cannulae, according to some embodiments of the present invention.

In some embodiments, the sensing of glucose levels and the dispensing of insulin can be done through separate exit ports, using two cannulae, both inserted into the subcutaneous tissue, residing in the body, as shown in FIG. 2. The dispensing apparatus (1005) and sensing apparatus (106) have separate respective cannulae (66, 6). The dispensing apparatus (1005) can be configured to have features of an insulin pump (i.e., a reservoir, a driving mechanism, tubing, etc.) and a cannula (66). The sensing apparatus (1006) includes a reservoir containing isotonic fluid and a pump for dispensing the isotonic fluid through the permeable or semi-permeable cannula (6). This allows analyte concentration level measurements, as described above. In this embodiment, the processor-controller apparatus (1007) receives inputs from the sensing apparatus (1006) and/or from the patient/user (via a user control/remote control unit (1008) in the semi-closed loop configuration) and is configured to control the dispensing apparatus (1005) to deliver insulin through cannula (66) to regulate glucose levels. In this embodiment, the two cannulae (6, 66) are positioned one adjacent to the other. The dispensing apparatus can deliver insulin by other means (not shown in FIG. 2) in addition to or instead of a subcutaneous cannula, e.g., by micro-array of miniature needles or by any other trans-cutaneous delivery means such as electrical and/or ultrasound skin stimulation.

Figure 3:
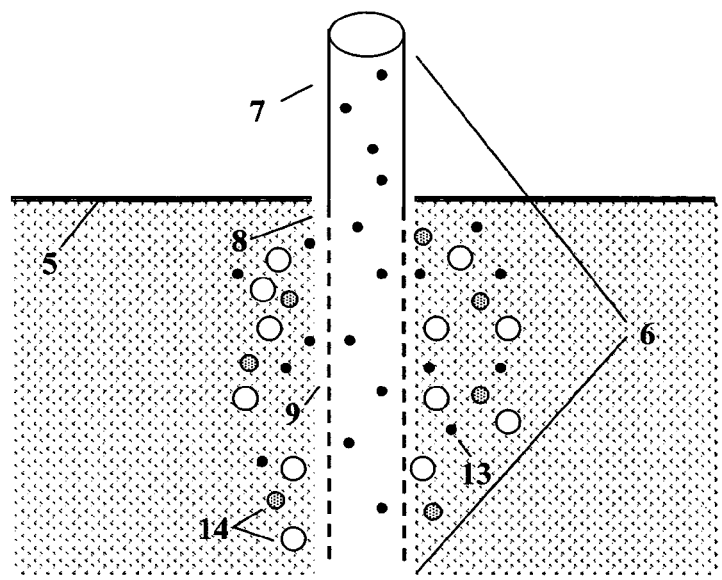
FIG. 3 illustrates an exemplary semi-permeable cannula and a diffusion process of molecules having variable weight, according to some embodiments of the present invention.

In some embodiments of the invention, the cannula that is used for sensing analyte concentration levels and for delivering fluid is semi-permeable, i.e., it allows diffusion of the analyte into the cannula through its wall. FIG. 3 illustrates an exemplary structure of the cannula (6), with its upper portion (7) and lower portion (8). The portions (7) and (8) are configured to be disposed above and below the skin, respectively. FIG. 3 also illustrates diffusion of substances through the cannula. The lower cannula portion (8) can include a semi-permeable membrane (9) that allows substances (13) of low molecular weight, and particularly, the desired analyte (e.g., glucose), to pass through pores of the semi-permeable membrane (9), and prevent substances (14) of higher molecular weight from passing through the pores of the member (9). The cannula (6) can be perfused with an analyte-free solution (e.g., insulin or saline) in order for diffusion to occur. Diffusion of analyte molecules occurs across the semi-permeable membrane (9), due to, for example, the initial concentration gradient. The diffusion process occurs in the direction of the concentration gradient, between the tissue fluid (e.g., ISF) and the solution within the cannula, until partial or full equilibrium between the inner and outer sides of the cannula is established. The outcome of the diffusion process is the presence of solution enriched by the analyte (i.e., the dialysate) inside the cannula (6) having an analyte concentration that is proportional or equal to the analyte concentration in the ISF. The analyte (e.g., glucose) concentration levels can be electrochemically measured either immediately in that portion of the cannula, which is inside the body (in the "intrinsecus" configuration), or by transporting the fluid above the skin and measuring the glucose concentration in a location outside the body (in the "extrinsecus" configuration).

Figure 4:
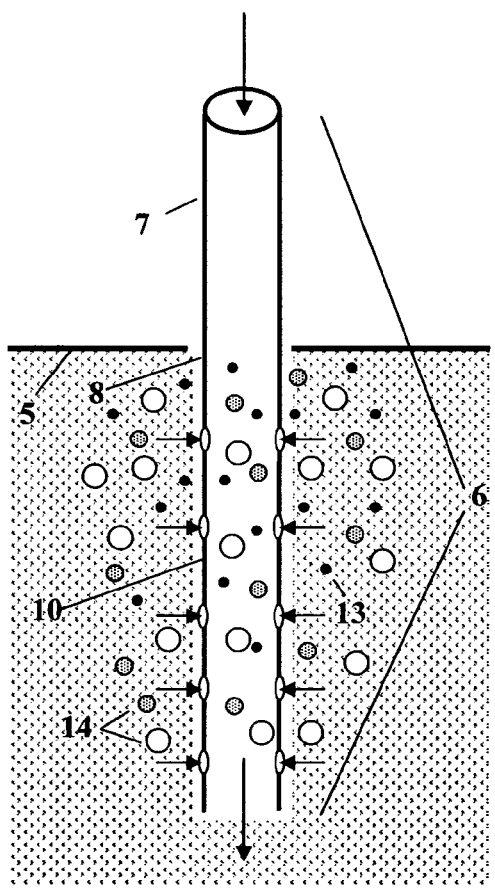
FIG. 4 illustrates an exemplary permeable cannula and a diffusion process of molecules having variable weight, according to some embodiments of the present invention.

In some embodiments of the invention, the cannula, which is used for sensing analyte concentration levels and delivering fluid, can be permeable. The permeability of the cannula is such that in addition to the diffusion of analyte molecules (13) from the ISF into the cannula (e.g., glucose), additional analytes contained in the ISF (14) can be diffused into the cannula. FIG. 4 illustrates another exemplary structure of the cannula (6) having upper portion (7) and lower portion (8) being disposed above and below the surface of the skin. FIG. 4 also illustrates diffusion of substances having variable molecular weight. The lower cannula portion (8) can be configured to include a permeable membrane (10) that allows the ISF to pass through pores of the membrane (10). The cannula (6) can be perfused with a solution (e.g., insulin or saline). Diffusion of ISF can occur across the permeable membrane (10) due to the initial concentration gradient. As shown in FIG. 4, the diffusion process occurs in the direction of the concentration gradient, between the tissue fluid (e.g., ISF) and the solution within the cannula, reaching partial or full equilibrium between the inner and outer sides of the cannula. The diffusion process results in the presence of a solution enriched by the analyte (i.e., the dialysate), inside the cannula (6) with an analyte concentration, which is proportional or equal to the analyte concentration in the ISF. An advantage of such cannula is that it has larger pores, which speed up diffusion of analyte into the cannula. Such pores also render manufacturing of the cannula cheaper and easier.

Figures 5A, 5B:
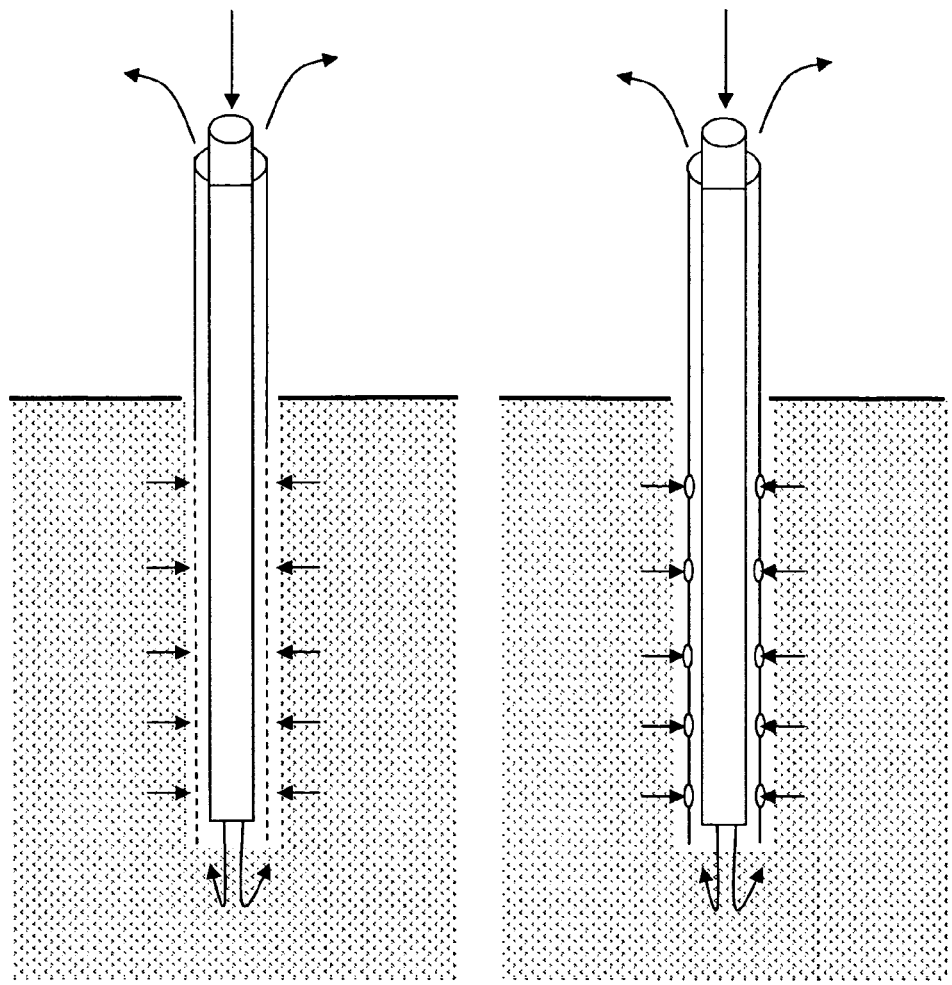
FIGS. 5a-b illustrate exemplary cannula suitable for microdialysis or microperfusion, according to some embodiments of the present invention.

In some embodiments, the cannula that is used for sensing analyte concentration levels and for delivering fluid can be a microdialysis or a microperfusion probe. The probe can be perfused with a solution (e.g., insulin or saline). In some embodiment, the probe can include an outer membrane that can be further configured to be semi-permeable or permeable. An exemplary microperfusion probe with a semi-permeable membrane is illustrated in FIG. 5a. An exemplary microperfusion probe with a permeable membrane is illustrated in FIG. 5b.

Figure 6:
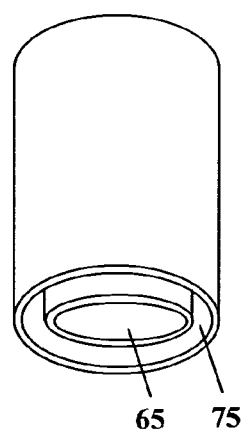
FIG. 6 illustrates an exemplary coaxial cannula, according to some embodiments of the present invention.

In some embodiments of the invention, the cannula (6) that is used for sensing analyte concentration levels and for delivering fluid is coaxial. In these embodiments, the cannula can be provided with an inner part (65) surrounded by an outer part (75), as illustrated in FIG. 6. The inner part (65) of the cannula (6) can be used to deliver fluid (e.g., insulin) and the outer part (75) can be used to sense analyte levels (e.g., glucose). In this case, the outer part of the cannula can be permeable or semi-permeable. In alternate embodiments, the inner part (65) can be used to sense analyte levels (e.g., glucose) and the outer part (75) can be used to deliver fluid (e.g., insulin).

Figure 7:
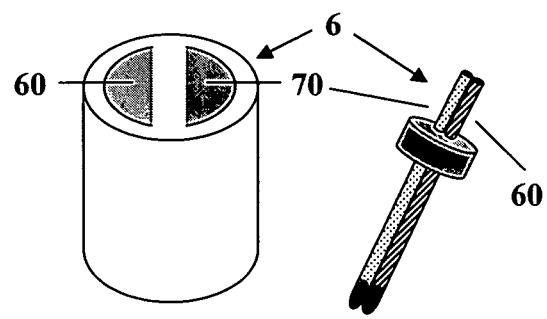
FIG. 7 illustrates an exemplary double lumen cannula, according to some embodiments of the present invention.

In another embodiment, the sensing of analyte (e.g., glucose) levels and the dispensing of fluid (e.g., insulin) are both carried out by a single double-lumen cannula, containing two compartments that can be separated by a partition. The double-lumen cannula is configured to include one compartment dedicated for sensing (60) and another compartment dedicated for dispensing (70). FIG. 7 illustrates an exemplary double-lumen cannula (6) with one compartment dedicated for sensing glucose (60) and the other compartment dedicated for dispensing insulin (70).

Figure 8:
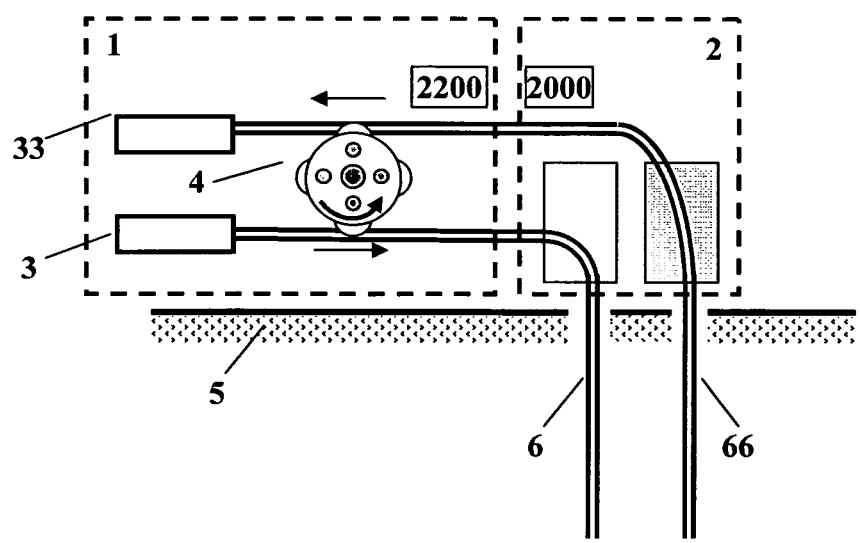
FIG. 8 illustrates an exemplary peristaltic pump with two tubes, corresponding to two separate cannulae—one for analyte sensing and the other for dispensing fluid, according to some embodiments of the present invention.

In some embodiments, the dispensing apparatus and the sensing apparatus can each include an independent cannulae (6, 66) and associated reservoirs (3, 33), but share a common peristaltic pump (4). The pump (4) can be configured to displace fluid in more than one tube in a space-saving configuration, as shown in FIG. 8. One tube can be configured to be a part of the sensing apparatus and further can be used to deliver fluid from the sensing cannula (66) to the electrochemical sensing unit (2000) and onto an electrical processing unit (2200) of the sensing apparatus, and then to the collecting reservoir (33). The other tube can be configured to be a part of the dispensing apparatus and further can be used to deliver fluid from the delivery fluid reservoir (e.g., insulin reservoir) (3) to the body of the patient via the delivery cannula (6). The dispensed and sensed fluids remain inside the separate tubing at all times. This feature of the present invention can be configured to prevent mixing of the fluids pumped from different reservoirs, and, thus, sufficiently reducing the risk of contamination, permitting control over the content and purity of the fluid delivered to the patient. In some embodiments, the collecting reservoir and the delivery fluid reservoir can be combined into a single reservoir (not shown).

In some embodiments, the fluid delivery device can be inserted into the body of the patient using a penetrating cartridge (501), which includes a penetrating member (502) and a cannula (6). In other embodiments, a "well" arrangement (503) can be used to provide fluid communication between the delivery tube (504) and the cannula (6) that is disposed in the subcutaneous tissue. The "well" arrangement (503) has an opening on the top, which can be closed by a sealing plug (505). When the penetrating cartridge (501) is inserted into the well arrangement (503), it pierces the sealing plug (505). The "well" arrangement (503) also includes an inlet port on its side and a channel, allowing passage of delivered fluid from the tube (504) to the cannula (6), though a lateral opening made in the cannula. An explanation of an exemplary well-arrangement mechanism and the penetrating cartridge can be found in a co-owned, co-pending U.S. patent application Ser. No. 11/397,115, the disclosure of which is incorporated herein by reference in its entirety.

Figure 9A:
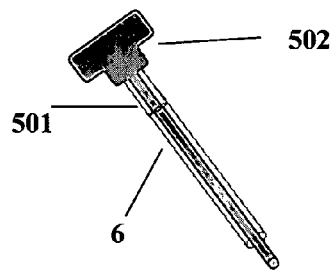
FIGS. 9a-d illustrate exemplary insertion of the cannula into the body of the patient through a well arrangement, using a penetrating cartridge, according to some embodiments of the present invention.
Figure 9B:
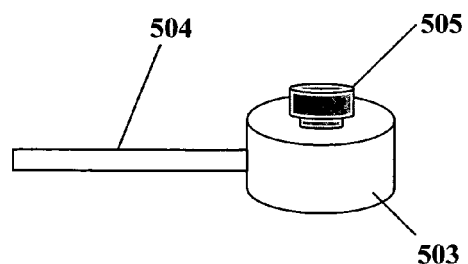
Figure 9C:
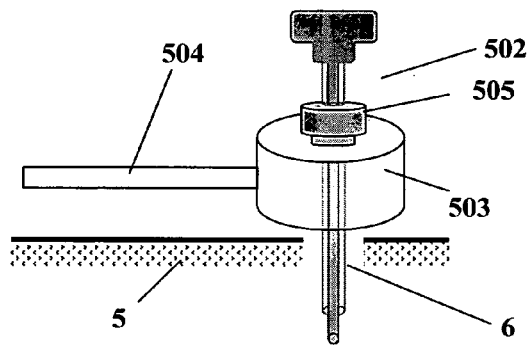
Figure 9D:
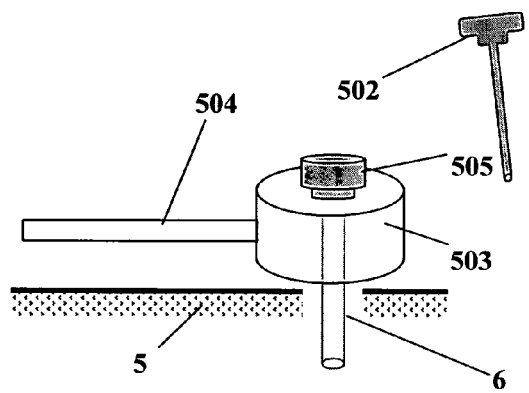

FIGS. 9a-d illustrate exemplary penetrating cartridge, according to some embodiments of the present invention. FIG. 9a illustrates a penetrating cartridge (501) prior to insertion into the well arrangement (503), where the penetrating cartridge (501) includes the penetrating member (502) and the cannula (6). FIG. 9b illustrates the well arrangement (503) prior insertion of the penetrating cartridge (501), where the well arrangement (503) includes the rubber plug (505) and the delivery tube (504). FIG. 9c illustrates the penetrating cartridge (501) and "well" arrangement (503), when the penetrating cartridge (501) is inserted (or penetrated) the skin (5) of the patient. FIG. 9d illustrates the cannula (6) being inserted into the skin (5), connected to the well arrangement (503), sealed by the rubber plug (505), connected to the delivery tube (504), and subsequent to removal of the penetrating member (502).

Figure 10A:
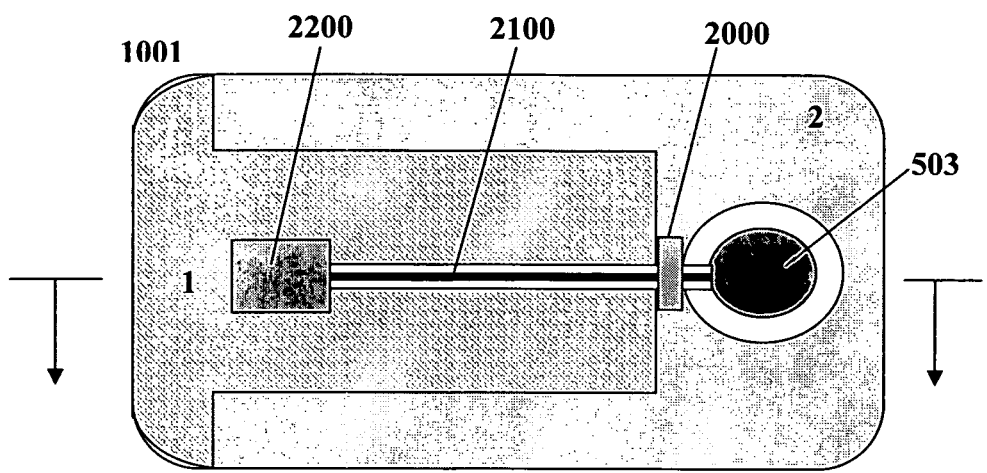
FIGS. 10a-b illustrate exemplary fluid delivery device having a reusable part and a disposable part, with electrochemical sensing components deployed in these parts, according to some embodiments of the present invention.
Figure 10B:
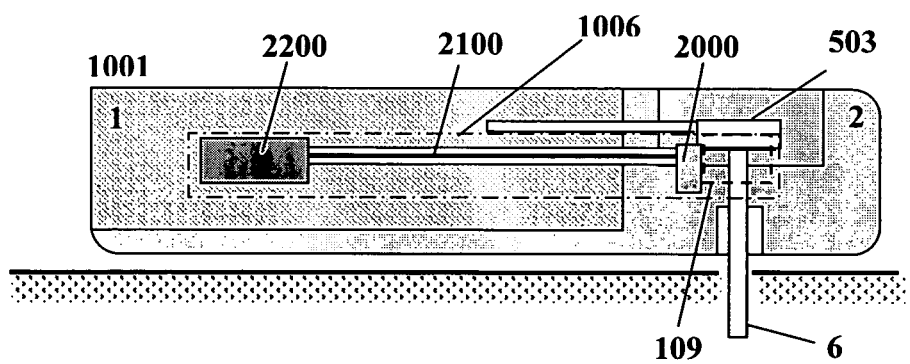

In some embodiments, the device (1001) can be configured to include two parts—a reusable part (1) and a disposable part (2), as shown in FIGS. 10a-b. FIG. 10a is an exemplary top view of the device (1001) having reusable part (1) and disposable part (2). FIG. 10b is an exemplary side view of the device (1001). The device (1001) can include an electrochemical sensing apparatus (1006). The sensing apparatus (1006) can include a plurality of units disposed in either in the reusable part (1) or the disposable part (2). In some embodiments, relatively expensive, non-disposable elements of the electrochemical sensing apparatus (1006) can be disposed in the reusable part (1) of the device (1001). The sensing apparatus (1006) can include a measuring cell (109), a sensing unit (2000) and an electronic processing unit (2200). The measurement cell (109), containing the analyte-rich fluid, and the sensing unit (2000), can be located in the disposable part (2). The sensing unit (2000) can be configured to include a transducer that is configured to produce an electrical signal, e.g., current, voltage (as shown by a line (2100)), based on an electrochemical reaction that occurs on such transducer. The signal is then transferred to the components of the electronic processing unit (2200), which is located in the reusable part (1).

Figure 11A:
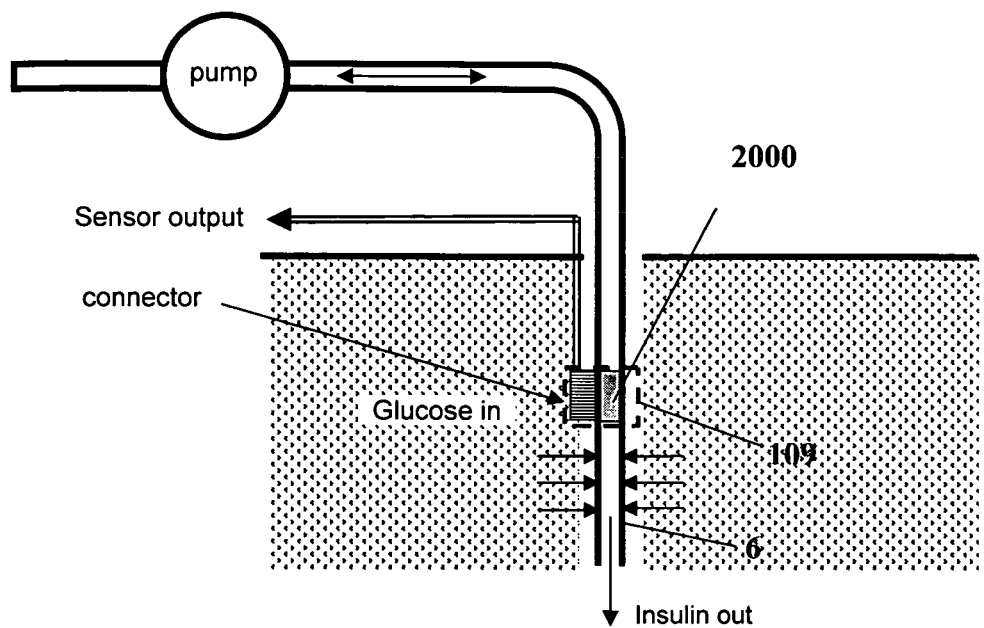
FIGS. 11a-b illustrate two exemplary configurations of the location of the measurement cell—"intrinsecus" and "extrinsecus" configurations, according to some embodiments of the present invention.
Figure 11B:
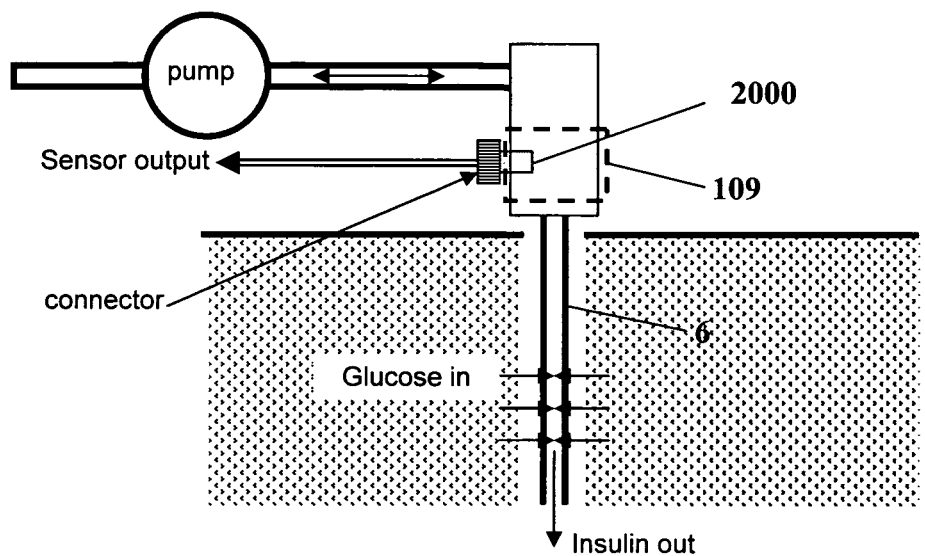

FIGS. 11a-b illustrate two exemplary locations of the measurement cell unit (109) and sensing unit (2000), according to some embodiments of the present invention. FIGS. 11a-b illustrate "intrinsecus" and "extrinsecus" location configurations, respectively. In an "intrinsecus" location configuration, the measurement cell unit (109) and sensing unit (2000) are associated with a portion of the cannula (6) that is located inside the body of the patient, as illustrated in FIG. 11a. In an "extrinsecus" location configuration, the measurement cell unit (109) and sensing unit (2000) are associated with a portion of the cannula (6) that is located above the skin (5) of the patient, as illustrated in FIG. 11b.

Figure 12A:
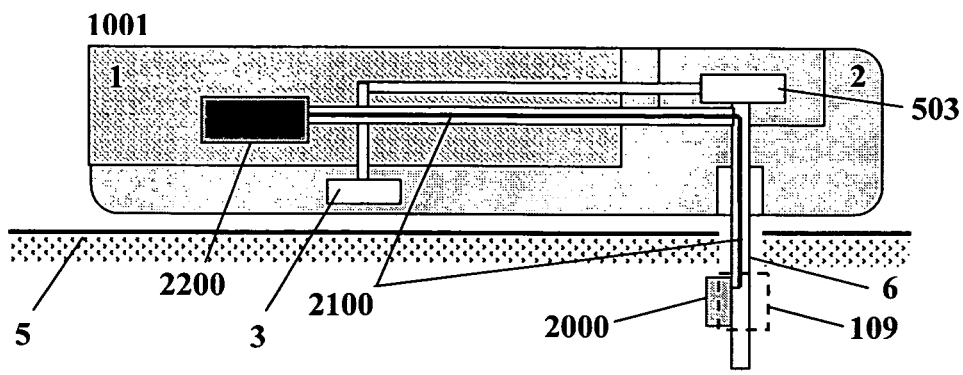
FIGS. 12a-b illustrate exemplary intrinsecus and extrinsecus configurations in a detailed view, as part of the whole system, according to some embodiments of the present invention.

FIG. 12a is a detailed view of an exemplary "intrinsecus" location configuration. The intrinsecus configuration includes a cannula (6) that penetrates the skin (5), and contacts the ISF. Once the analyte from the ISF is diffused into the solution within the cannula (6), the analyte-rich solution, residing in the "intrinsecus" measurement cell unit (109) is analyzed in the "intrinsecus" sensing unit (2000). In this configuration, the measurement cell unit (109) and the sensing unit (2000) are both located in a portion of the cannula (6) that is below the skin, as shown in FIG. 12a. The cannula (6) can also be connected to the reservoir (3) via the "well" arrangement (503). In the "intrinsecus" configuration, the cannula (6), the reservoir (3), the "well" arrangement (503), the measurement cell unit (109), and the sensing unit (2000) are all located within the disposable part (2) of the device (1001). The pump (not shown in FIG. 12a), the electronic processing unit (2200) of the sensor and all the pump electronics are located in the reusable part (1) of the device (1001).

In some embodiments, the measurement cell unit (109) and one or more components of the sensing unit (2000) are located "intrinsecusly" in a part of the cannula (6) that is located inside the body of the patient, e.g., the working electrode, the electrochemical reaction. Additionally, one or more components of the sensing unit (2000) can be located outside the body of the patient, i.e., "extrinsecusly". Such extrinsecus components can include the counter electrode, the reference electrode, the transduction of the chemical reaction to an electrical signal.

Figure 12B:
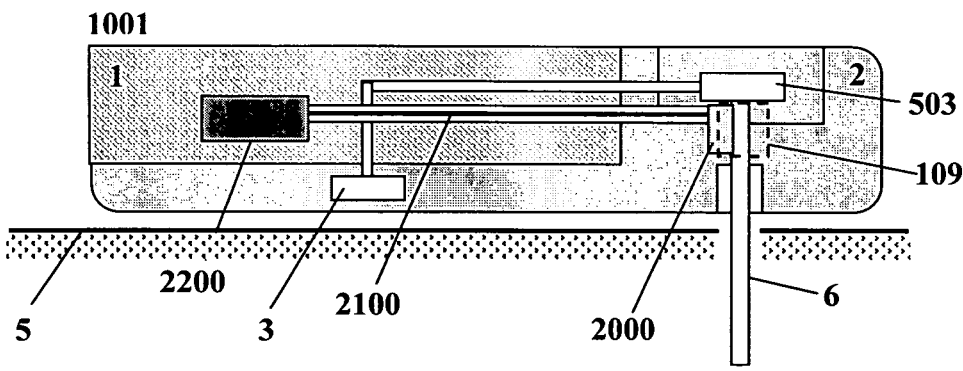

FIG. 12b is a detailed view of an exemplary "extrinsecus" location configuration, according to some embodiments of the present invention. This configuration includes cannula (6) that is configured to penetrate the skin (5) of the patient and contact the ISF. Once the analyte from the ISF diffuses into the solution within the cannula (6), the analyte-rich solution is transported from the cannula (6) residing in the body, to the "extrinsecus" measurement cell unit (109), and analyzed by an "extrinsecus" sensing unit (2000). In this configuration, the measurement cell unit (109) and the sensing unit (2000) are both located in a portion of the cannula (6) that is above the surface of the skin (5). In an "extrinsecus" configuration embodiment, in order to transport analyte-rich fluid from the cannula (6) to the measurement cell unit (109), a pump (not shown in FIG. 12b) within the device (1001) can be used to pump the fluid up and down the cannula (6). Further, oxygen can be used to facilitate electrochemical reaction to overcome a problem of stoichiometric oxygen deficit in the body. Alternatively, mediators can be used to facilitate an electrochemical reaction and overcome a potential leaching and toxicity of the mediator by disposing of them outside the body of the patient.

Figure 13:
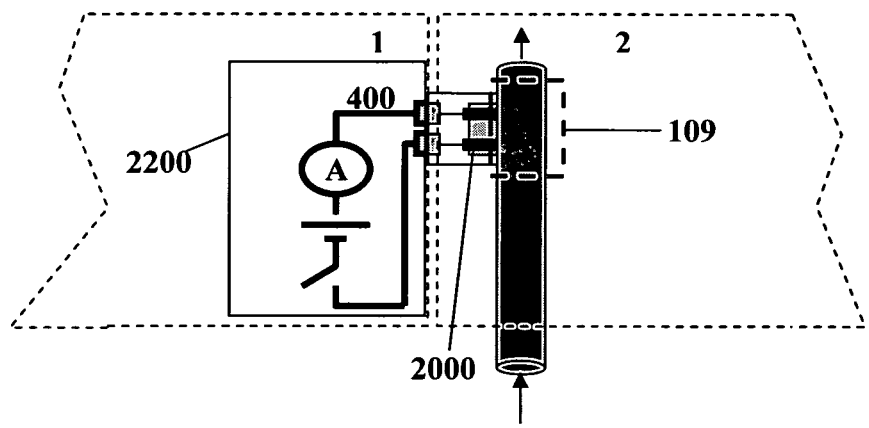
FIG. 13 illustrates exemplary division of the sensing apparatus components within the disposable and reusable parts, according to some embodiments of the present invention.

FIG. 13 illustrates an exemplary device (1001) having components of the sensing apparatus disposed in the reusable part (1) and disposable part (2). As illustrated, the measuring cell unit (109) and the sensing unit (2000) are disposed in the disposable part (2). Whereas, the electronic processing unit (2200) is disposed in the reusable part (1). The unit (2200) can be configured to include an amperometric circuit (400). Once the reusable part (1) and the disposable part (2) are coupled together, the amperometric circuit is closed. Without such coupling, a signal corresponding to the current produced by the electrodes of the sensing unit (2000) cannot be generated.

Figure 14A:
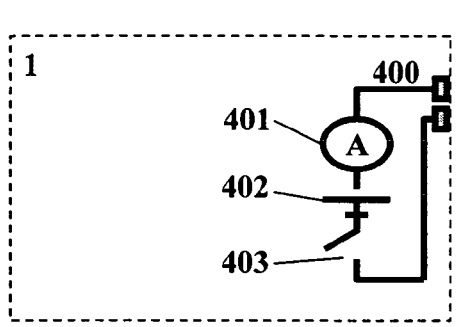
FIGS. 14a-b illustrate an exemplary division of the sensing apparatus components within the disposable and reusable parts, according to some embodiments of the present invention.
Figure 14B:
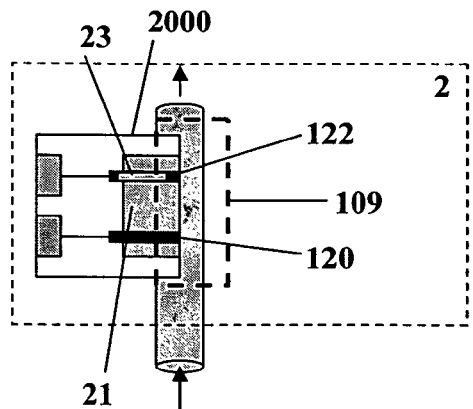

FIGS. 14a-b illustrate an exemplary sensing apparatus, according to some embodiments of the present invention. The sensing apparatus is configured to include an electronic processing unit. Such electronic processing unit can be further configured to include the amperometric circuit (400). The circuit (400) includes an amperometer (401), a battery (402), and a switch (403), as illustrated in FIG. 14a. As shown in FIG. 14b, the sensing unit (2000) further includes a working electrode (122) that is located in the disposable part (2) of the device (1001). During operation, electrons from the working electrode (122) flow towards a positive pole of the battery (402) and the current generated by this flow is measured by the amperometer (401). The switch (403) is configured to close the circuit when as desired. As such, the current passes through the circuit (400) only when measurements are being carried out, thereby, saving energy. As further shown in FIG. 14b, the electrodes can be configured to provide electrochemical sensing during operation of the sensing apparatus of the device (1001). Electrodes can include an insulating base layer (21) for a plurality of layers deployed on it and serve as a substrate for the electrodes. The insulating base layer (21) can be manufactured from ceramics; glass, Goretex, or any other suitable material.

In some embodiments, a working electrode (122) can be located on the base layer (21). The working electrode (122) can be the electrode on which electrochemical reaction(s) take place during operation of the device (1001). The working electrode can include an enzyme that is capable to catalyze analyte oxidation and reduction. In some embodiments, such oxidation and/or reduction can be performed using a mediator, such as, an electron transfer agent. During a redox (i.e., reduction/oxidation) reaction taking place on the working electrode, at least one electron can be released. As a result, current is generated by the electrode, which is detected using amperometer (401). Such current can be measured based on oxidation and/or reduction of an electro-active compound at the working electrode. In some embodiments, the base layer (21) can be configured to serve as the working electrode (122), in which case the cannula itself can serve as the insulating substrate.

In some embodiments, an analyte sensing layer (23) can be provided on the working electrode (122). The analyte sensing layer (23) includes an enzyme used in the catalytic reaction (e.g., GOX, hexokinase, glucose dehydrogenase) or any other enzyme. The analyte sensing layer (23) can be configured to include a plurality of enzymes (e.g., GOX, catalase, or other). The analyte sensing layer (23) can be also secured to the working electrode (122) using immobilization techniques, such as cross-linking, entrapment, or any other techniques. Immobilization of the enzyme enables maximum contact with the working electrode, which serves as the transducer, and, thus, a maximum response is also achieved.

In some embodiments, a counter electrode (120) can be paired with the working electrode (122). Currents of opposite signs are configured to pass through the two electrodes and the voltage of the counter electrode (120) can be controlled accordingly. The counter electrode (120) can also be formed on the analyte sensing layer (23). The sensing layer can be configured to include additional components (not shown in FIGS. 14a-b) such as a modulating layer that modulates the diffusion of one or more analytes (e.g., such modulating layer may facilitate the diffusion of oxygen, allowing excess of oxygen for the GOX reaction). Additionally, a reference electrode can be used in measuring the working electrode potential. In some embodiments, a reference electrode can be configured to have a constant electrochemical potential as long as no current flows through it. As can be understood by one skilled in the art, the reference electrode can be configured to have any potential.

Figure 15A:
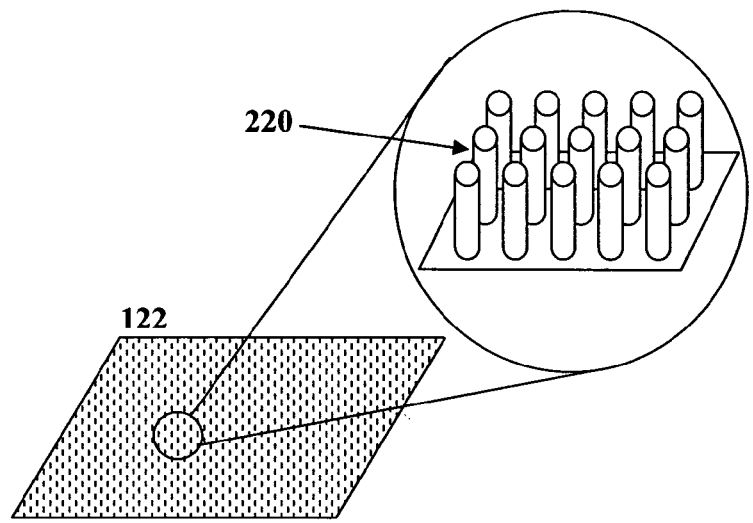
FIGS. 15a-b illustrate exemplary increases in the surface area of the working electrode, according to some embodiments of the present invention.
Figure 15B:
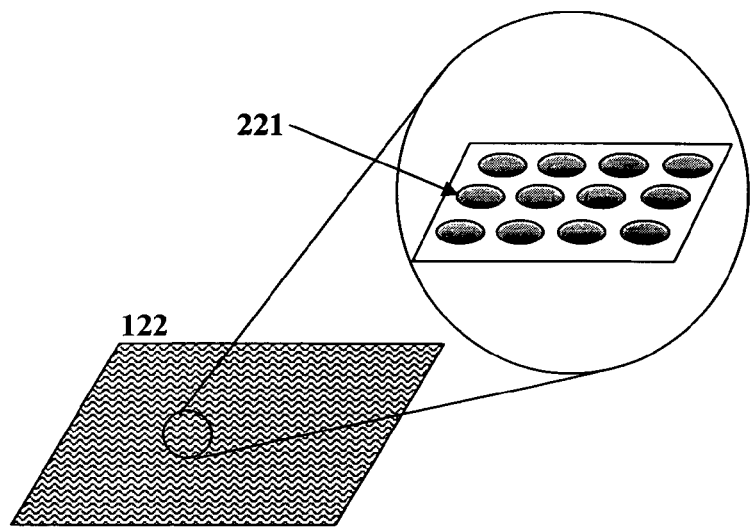

In some embodiments, the working electrode can include a region having a non-flat surface area. In these embodiments, a contact between the analyte and the working electrode is enhanced due to increase of the surface area. The non-flat electrode area can further include a plurality of fins with a fractal shaped surface, or any other type of surface. Such surfaces can be manufactured using particle deposition, by etching out of craters in the surface, or by any other methods. FIGS. 16a-b illustrate exemplary increased surface areas between the analyte sensing layer (containing the enzyme) and the electrochemical transducer. FIG. 15a illustrates exemplary nanostructures (220) configured to protrude out from the electrode (122). FIG. 15b illustrates exemplary grooves or holes (221) that can be fabricated within the electrodes. An increased surface area between the analyte sensing layer (containing the enzyme) and the electrochemical transducer (specifically, the working electrode) can improve performance of sensors due to the possibility of loading more enzyme(s). The increased surface area also facilitates electron transfer between the enzyme active site and the transducer. Thus, the greater the surface area, the more particles can collide with the area per second, thereby, generating higher reaction rate.

Figure 16:
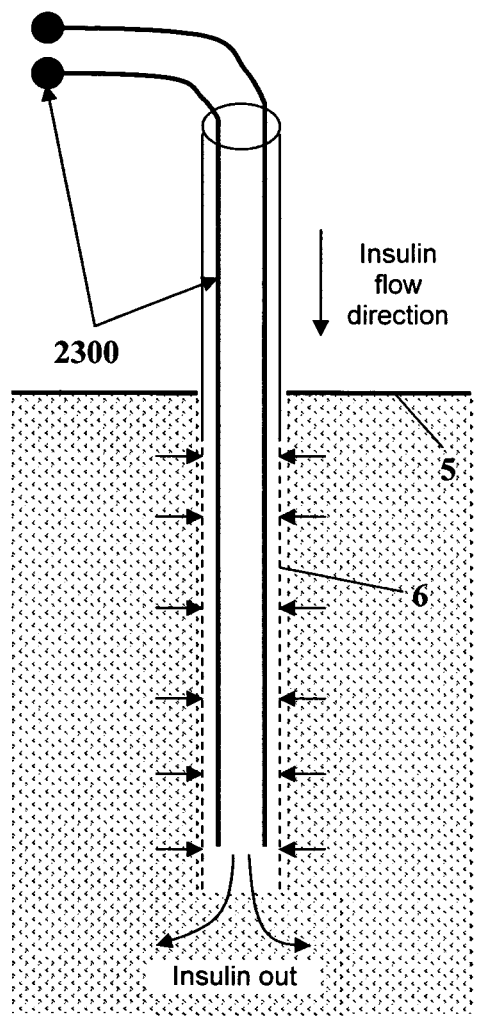
FIG. 16 illustrates exemplary cannula of the device as a single tube having sensing electrodes, in an "intrinsecus" configuration, according to some embodiments of the present invention.
Figure 17:
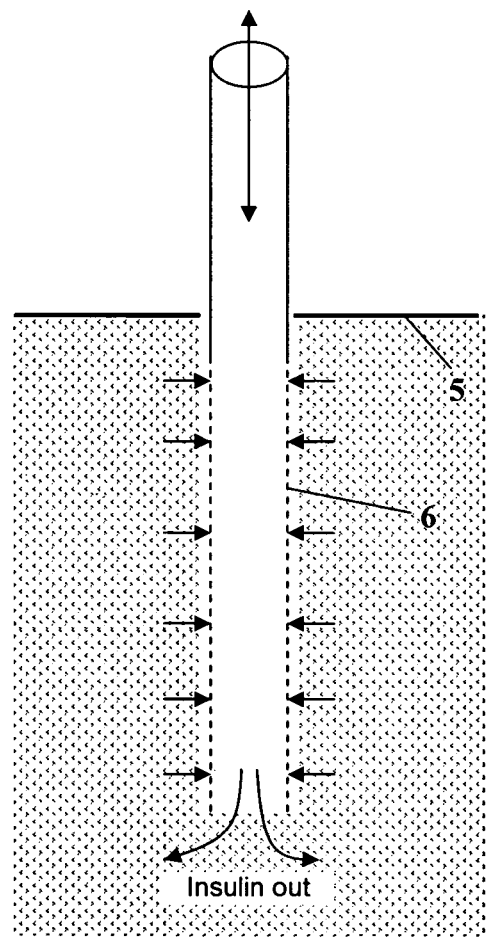
FIG. 17 illustrates exemplary cannula of the device as a single tube with reciprocating flow, in an "extrinsecus" configuration, according to some embodiments of the present invention.

In the embodiment of "intrinsecus" location configuration, cannula (6) can be configured as a single tube having a pair of sensing electrodes (2300). The sensing electrodes (2300) can be a part of the electrochemical sensing unit. FIG. 16 illustrates an exemplary single cannula (6) having sensing electrodes (2300). In such embodiments, electrodes (2300) can be deposited on the inner surface of the cannula (6). In the embodiment of "extrinsecus" configuration, cannula (6) can be configured as a single tube suitable for reciprocating flow of a fluid therethrough. Insulin can be configured to be delivered through the cannula (6) and to flow in one direction. An analyte-rich solution, after diffusion of the analyte into the solution within the cannula (6), can be transported in the opposite direction—upward towards the measurement cell unit, as shown in FIG. 17. The measurement cell unit and the sensing unit (not shown in FIG. 17) are located in an "extrinsecus" configuration, i.e., above the skin of the patient. To transport the analyte-rich fluid up the cannula (6) to the measurement cell unit in this configuration, a pump can be used for pumping the fluid up and down the cannula. As such, a reciprocating flow can be allowed. In some embodiments, the cannula can be configured as a microdialysis or a microperfusion probe, as shown in FIGS. 5a-b. As stated above, the probe can be perfused with a solution (e.g., insulin, saline, or any other solution). The measurement cell unit and the sensing unit (not shown) can be arranged in the "extrinsecus" location configuration. To perfuse the probe with such solution, a pump can be used to create a microdialysis or a microperfusion flow.

Figure 18:
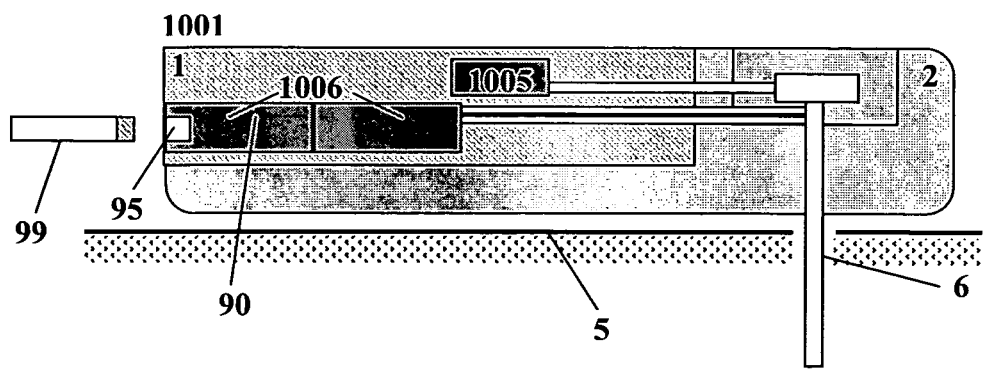
FIG. 18 illustrates an exemplary glucometer, which uses a blood glucose test strip, incorporated into the device, according to some embodiments of the present invention.

In some embodiments, a blood glucose monitor or any glucometer means (90), which uses a blood glucose test strip (99) to determine glucose levels in the blood, can be incorporated into the device. In these embodiments, the device (1001) includes the dispensing apparatus (1005) and the sensing apparatus (1006) as described above, where the sensing apparatus (1006), in addition to its ability to perform sensing of analytes in the ISF, can include glucometer means (90), enabling it to sense analytes in the blood. FIG. 18 illustrates such exemplary glucometer means (90) and test strip (99) incorporated into the device (1001), according to the present invention.

The glucometer means (90) can be a part of the sensing apparatus (1006), and it can be disposed in the reusable part (1) of the device (1001). The lateral wall of the device (1001), at the location where the glucometer means (90) is disposed, can be provided with an opening (95) through which a test strip (99) can access the glucometer means (90). The patient/user can extract blood from a remote location in the body, and place the blood on the test strip (99). The test strip (99) is then inserted into the device (1001) through the designated opening (95) in the glucometer means (90).

In some embodiments, the glucometer means (90) with the blood glucose test strip (99) can calibrate the sensing apparatus. Continuous glucose monitoring systems can be calibrated relative to known glucose values in order to maintain accurate glucose measurements throughout their operation. As such, device (1001) can further include a dispensing apparatus (1005), a sensing apparatus (1006) and a calibration apparatus having a blood glucose monitor (or any glucose monitoring means) (90) with a blood glucose test strip (99).

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed:

1. A system for delivering fluid to and sensing concentration levels of an analyte in a body of a patient, comprising:
   a dispensing apparatus configured to infuse fluid into the body of the patient; and
   a sensing apparatus configured to be in communication with said dispensing apparatus and further configured to detect a concentration level of the analyte in the body of the patient;
   wherein the dispensing apparatus and the sensing apparatus share a single fluid reservoir, a single pump, and a single cannula with one single exit port; and
   wherein the system further comprises a processor-controller apparatus configured to receive input data from the sensing apparatus and, after processing the input data, authorize the dispensing apparatus to dispense fluid based on the detected level of the analyte in the body of the patient and an external input.

2. The system according to claim 1, further comprising:
   a remote-controlled unit configured to control said dispensing apparatus; and
   another remote-controlled unit configured to control said sensing apparatus;
   wherein said another remote-controlled unit is configured to transmit information to said remote-controlled unit to adjust dispensing of fluid to the body of the patient.

3. The system according to claim 1, wherein said analyte is glucose and said fluid is insulin.

4. The system according to claim 1, further comprising:
a reusable part; and
a disposable part configured to be coupled to said reusable part;
wherein said reusable part is configured to include electronics and a driving mechanism of said dispensing and sensing apparatuses, and said disposable part is configured to include a fluid reservoir and a needle assembly of said dispensing and sensing apparatuses; whereby upon coupling of said reusable part and said disposable part, said dispensing and said sensing apparatuses become operable.

5. The system according to claim 4, wherein said sensing apparatus is a skin patch configured to include a cannula insertable into a subcutaneous tissue.

6. The system according to claim 1, further comprising:
a needle assembly having a cannula and a penetrating member;
wherein the sensing apparatus is an electrochemical sensing apparatus, and the processor-controller apparatus includes a processor; and
wherein said processor and said pump are configured to control flow of fluid from said reservoir into said cannula.

7. The system according to claim 6, wherein at least a portion of said cannula is permeable to said analyte to enable diffusion of the analyte into said cannula.

8. The system according to claim 1, wherein said pump is a peristaltic pump.

9. The system according to claim 1, wherein said pump is a syringe.

10. The system according to claim 1, wherein said sensing apparatus is configured to include an electrochemical detection mechanism having a sensor.

11. The system according to claim 10, wherein said sensor is selected from a group consisting of: an enzymatic assays sensor, a non-enzymatic analyte sensor.

12. The system according to claim 10, wherein said electrochemical detection mechanism includes
a working electrode;
a counter electrode;
a measurement cell unit configured to include an analyte-saturated fluid configured to contact said working electrode;
wherein said measurement cell unit is configured to generate a flow of current between said working electrode and said counter electrode; and
wherein said electrochemical detection mechanism, based on said flow of said current, is configured to determine said level of concentration of analyte in the body of the patient.

13. The system according to claim 12, wherein said measurement cell unit is located in a portion of the cannula which in use is located within the body of the patient.

14. The system according to claim 12, wherein said measurement cell unit is located in a portion of the cannula which in use is located outside the body of the patient.

15. The system according to claim 14, wherein the sensing unit is configured to be located in use outside the body, above the skin.

16. The system according to claim 15, wherein the pump is configured to transport analyte-rich solution from the cannula to the measurement cell unit for analysis.

17. The system according to claim 4, further comprising an electrical circuit configured and arranged such that a signal representing the concentration level of the analyte detected by the sensing apparatus cannot be generated without the coupling of the reusable and disposable parts.

18. The system according to claim 17, wherein the electrical circuit is an amperometric circuit comprising an amperometer.

19. The system according to claim 18, wherein the electrical circuit further comprises a switch configured to close the circuit only when measurements are being carried out by the sensing apparatus.

* * * * *

UNITED STATES PATENT AND TRADEMARK OFFICE
CERTIFICATE OF CORRECTION

PATENT NO.       : 8,603,075 B2                              Page 1 of 1
APPLICATION NO. : 11/989665
DATED            : December 10, 2013
INVENTOR(S)      : Yodfat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1112 days.

Signed and Sealed this
Twenty-second Day of September, 2015

Michelle K. Lee
*Director of the United States Patent and Trademark Office*